United States Patent [19]

Hiji

[11] Patent Number: 4,629,725

[45] Date of Patent: Dec. 16, 1986

[54] METHOD FOR INHIBITING INCREASE IN BLOOD SUGAR CONTENT

[76] Inventor: Yasutake Hiji, c/o Tottori University School of Medicine 86, Nishi-machi, Yonago-shi, Tottori-ken, Japan

[21] Appl. No.: 712,507

[22] Filed: Mar. 22, 1985

Related U.S. Application Data

[63] Continuation-in-part of Ser. No. 545,335, Oct. 25, 1983, abandoned.

[30] Foreign Application Priority Data

Oct. 25, 1982 [JP]  Japan ................................ 57-187037

[51] Int. Cl.4 ........................................... A61K 31/715
[52] U.S. Cl. ....................................... 514/60; 514/23; 514/53; 514/54
[58] Field of Search ..................... 536/1.1; 514/23, 54, 514/60, 53

[56] References Cited

U.S. PATENT DOCUMENTS

3,931,146  1/1976  Kato et al. ........................... 536/1.1
4,370,472  1/1983  Igarashi et al. ...................... 536/1.1

*Primary Examiner*—Johnnie R. Brown
*Attorney, Agent, or Firm*—Armstrong, Nikaido, Marmelstein & Kubovcik

[57] ABSTRACT

A method of inhibiting the increase in blood sugar content which usually arises from intake of foodstuff containing starch and/or sucrose by adding pullulan to the foodstuff in a weight ratio of pullulan to starch and/or sucrose of 1:400 to 1:20.

Also, a foodstuff product containing starch and/or sucrose to which pullulan is added in a weight ratio of pullulan to starch and/or sucrose of 1:400 to 1:20.

1 Claim, 5 Drawing Figures

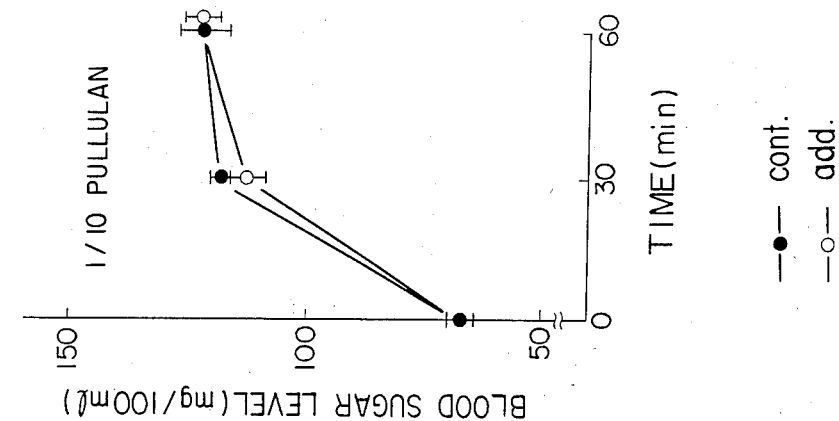
FIG. 1-A
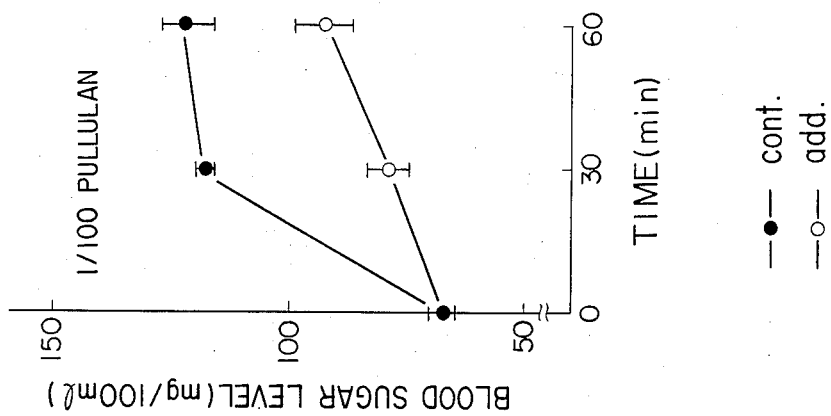
FIG. 1-B
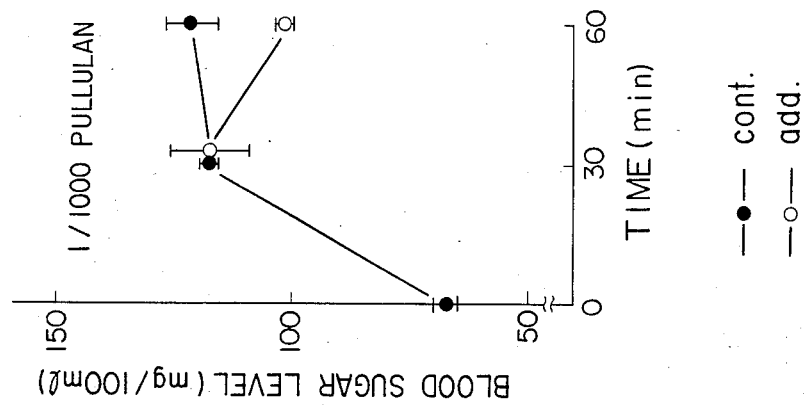
FIG. 1-C

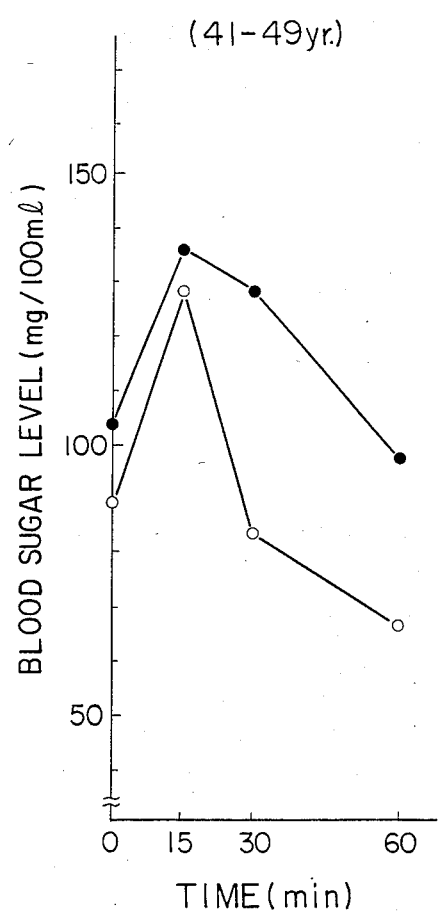
FIG. 2-A
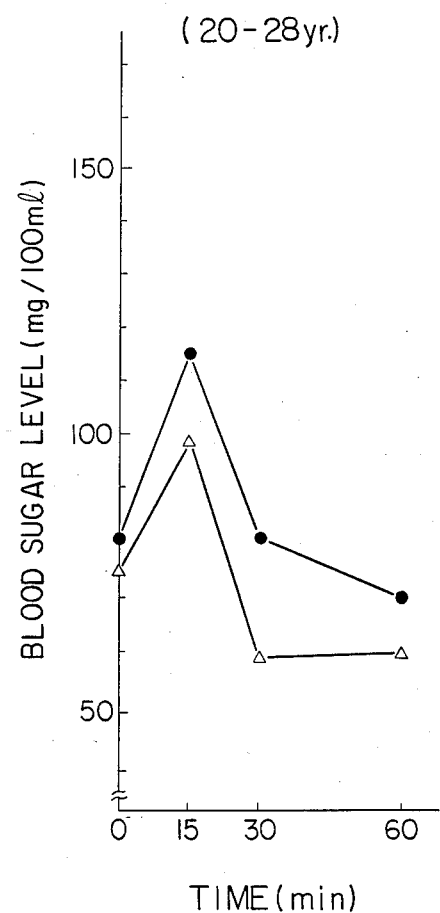
FIG. 2-B
— CONTROL 25g SUCROSE /500ml  — CONTROL 25g SUCROSE/500ml
—○— 1/50 PUL(25g SUC+0.5gPUL)/500ml —△— 1/25PUL(25gSUC+1.0gPUL)/500ml

METHOD FOR INHIBITING INCREASE IN BLOOD SUGAR CONTENT

This application is a continuation-in-part of application Ser. No. 545,335, filed on Oct. 25, 1983 and abandoned as of Apr. 18, 1985.

BACKGROUND OF THE INVENTION

This invention relates to a method for inhibiting increase in blood sugar content, and a foodstuff product containing a hyperglycemia controlling agent.

Various studies have been heretofore conducted with the goal of inhibiting the intestinal absorption of glucose in order to control the increase in blood sugar content which arises from intake of sucrose and starch, in order to prevent obesity in a normal person or to implement the diet therapy of a diabetic person. However, these studies have not yielded satisfactory results. Applicant has conducted various investigations of hyperglycemia controlling agents which can control the increase in blood sugar content which usually arises from intake of sucrose and starch. As a result of these investigations, applicant has found that polymers which comprise glucose molecules repeatedly bonded by $\alpha$-1,6-bonds can exhibit a controlling effect on the increase in blood sugar content. One such compound is isomaltotriose, which is an oligosaccharide consisting of three glucose molecules bonded by $\alpha$-1,6-bonds. When isomaltotriose is added in a weight ratio of 1:400 to the sucrose intake, it is found that only 20% of the sugar intake is absorbed through the intestinal tract. Similar effects are also observed in other $\alpha$-1,6-bonded polysaccharides such as dextran.

The toxicity of a food additive is always of great concern. In this respect, isomaltotriose is not a desirable food additive because, even though it inhibits the absorption of sucrose through the intestinal tract, it is itself absorbed through the intestinal tract. Dextran is also not a desirable food additive because it depresses the function of blood platelets, thereby prolonging blood coagulation time. Dextran also has a number of other undesirable side effects.

SUMMARY OF THE INVENTION

An object of this invention is to provide a non-toxic, safe method for inhibiting the intestinal absorption of sucrose and starch, and thereby control the increase in blood sugar content which usually arises from the intake of sucrose or starch. The method of this invention uses pullulan as a hyperglycemia controlling agent.

Another object of this invention is to provide a foodstuff product which contains pullulan as a component effective in inhibiting the increase in blood sugar content arising from the intake of sucrose or starch contained in the foodstuff.

BRIEF DESCRIPTION OF THE DRAWINGS

FIGS. 1-A, B and C show the changes in blood sugar content with time for three groups of rats, each group being fed with sucrose mixed with pullulan in a different ratio.

FIGS. 2-A, B show the respective optimum weight ratio of pullulan to sucrose for obtaining the largest controlling effect on the increase in blood sugar content in two groups of persons of different ages.

DESCRIPTION OF PREFERRED EMBODIMENTS

Pullulan is a naturally occurring polysaccharide which was first manufactured in 1978 on a commercial basis. Pullulan has been used in food processing and, by virtue of its indigestibility by the endogenic digestive enzymes, it has also been used in low-calorie diets.

Pullulan is a polymer containing glucose molecules bonded by $\alpha$-1,6-bonds. Therefore, pullulan belongs to the group of compounds which have a hyperglycemia controlling effect, according to the applicant's discovery. However, since the $\alpha$-1,6-bonded portion of the pullulan molecule constitutes only 30% of the compound, the remaining portion being $\alpha$-1,4-bonded, pullulan does not have a hyperglycemia controlling effect as strong as that exhibited by other $\alpha$-1,6-bonded compounds. However, pullulan shows no toxicity in acute, semi-acute, and chronic toxicity tests, and no abnormalities are found in the internal organs of the test animals administered pullulan. Therefore, pullulan is considered a safe food additive. Furthermore, its chemical properties are not affected by changes in pH or by heat, so that pullulan is expected to fully withstand processes such as cooking and food processing.

Applicant has also discovered that pullulan has the effect of inhibiting only the increase in blood sugar content arising from intake of sucrose or starch. Pullulan was found to have no similar effect against the increase in blood sugar content arising from intake of glucose or maltose.

The mechanism by which pullulan inhibits the increase in blood sugar content which usually arises from intake of sucrose or starch is not known. It is clear, however, that pullulan does not serve as an inhibitor for sucrose-decomposing enzymes present in the epithelial cells of the intestinal tract, as proved by experiments conducted by applicant using enzymes extracted from intestinal tracts. It is also certain that the hyperglycemia controlling effect of pullulan cannot be attributed to abnormal secretion of insulin, since this controlling effect was not observed with glucose or maltose.

In the method of this invention, pullulan is added to foodstuff containing sucrose, starch and mixtures thereof in a weight ratio of pullulan to sucrose, starch and mixtures thereof in the range of 1:400 to 1:20.

The foodstuff products of this invention are prepared by incorporating pullulan into any foodstuff containing sucrose, starch and mixtures thereof, by means of any mechanical mixing method, and in a ratio of pullulan to sucrose, starch and mixtures thereof in the range of 1:400 to 1:20. The foodstuff products of this invention include any food or beverage suitable for human consumption.

The present invention is illustrated below by reference to examples.

EXAMPLE 1

48 Wistar strain rats were orally administered sucrose in an amount of 1.9 g/per kg of body weight. The fasting blood sugar content of the rats was 79.2±11.6 mg/100 ml. The blood sugar content increased to a maximum of 143.9±16.5 mg/100 ml, 60 minutes after the intake of sucrose. The blood sugar content decreased to almost the normal level 120 minutes after the intake of sucrose.

When 5 mg of pullulan of a molecular weight of 70,000 was added to the sucrose intake, corresponding to a weight ratio of 1:400 of pullulan to sucrose, the blood sugar content increased to only 119.3±25.4 mg/100 ml, 60 minutes after the sucrose intake. Thus, it was found that the increase in blood sugar content which usually arises from the intake of sucrose can be inhibited by administering pullulan with the sucrose.

EXAMPLE 2

The experiment described in Example 1 was repeated with the exception that starch was administered instead of sucrose. Rats having a fasting blood sugar content of 49.2±7.2 mg/100 ml, when orally administered 1 g of starch per kg of body weight, exhibited a gradual elevation in blood sugar content to a level of 109.0±11.0 mg/100 ml after 30 minutes.

When 50 mg of pullulan (corresponding to 1/40 of weight of starch) was added to the starch, the blood sugar content was 82.3±12.3 mg/100 ml after 30 minutes. Thus, it was found that the increase in blood sugar content which usually arises from the intake of starch could be inhibited by administering pullulan.

EXAMPLE 3

Wistar strain rats (each weighing 50 to 60 grams) were fed with a commercial diet to which 20% by weight of pullulan had been added. The commercial diet contained 51% carbohydrates, such as cornstarch and granulated sucrose. A difference in weight arose between the group of rats fed with the pullulan-containing diet and the group fed with a pullulan free diet. This difference began to arise after about ten days. The weight on the sixtieth day of feeding was 307±21 g for the control group, and 270±18.5 g for the group administered the diet containing 20% pullulan. Thus, it was found that pullulan was effective in controlling weight gain.

EXAMPLE 4

The effect of the oral administration of pullulan (molecular weight 17,500) was examined on nine human male subjects. When sugared water prepared by dissolving 100 g of sucrose in 500 ml of water was administered to a subject having a fasting blood sugar content of 74.9±6.1 mg/100 ml, his blood sugar content increased to 140±8.6 mg/100 ml after 30 minutes.

On the other hand, when 5 grams of pullulan (corresponding to a weight ratio of 1:20 of pullulan to sucrose) was added to the above sugared water, the blood sugar content in the same person after 30 minutes was 109.2±17.2 mg/100 ml. As expected, variations were observed in the effect of pullulan in different individuals. It was noted that in the case of a person in whom pullulan had a strong controlling effect, the blood sugar content was maintained at a level that was almost as low as the fasting blood sugar content. Moreover, it was found that the effect of pullulan in persons in whom pullulan did not have a marked effect can be optimized by varying the amount of pullulan. Thus it was clear that the optimal amount of pullulan varies with each individual.

EXAMPLE 5

The same procedure as in example 4 was repeated with two prediabetes-prone persons. One person had a fasting blood sugar content of 85 mg/100 ml and their blood sugar level after 60 minutes from the administration of sugared water of 148 mg/100 ml. However, his blood sugar content after 60 minutes was maintained at 92 mg/100 ml when pullulan-containing sugared water was used.

The other person had a fasting blood sugar content of 100 mg/100 ml, and a blood sugar content 120 minutes after the administration of sugared water of 142 mg/100 ml. However, his blood sugar content after 120 minutes could be maintained at 124 mg/100 ml when pullulan-containing sugared water was used.

EXAMPLE 6

Wistar strain rats divided into three groups were orally administered sucrose containing pullulan of a molecular weight of 17,500 in a weight ratio of pullulan to sucrose of 1:1000 for the first group (FIG. 1-A), 1:100 for the second group (FIG. 1-B) and 1:10 for the third group (FIG. 1-C). The change in blood sugar content (mg/100 ml) with time was observed for each group of rats, and compared with the changes in blood sugar content in control groups of rats which were fed sucrose containing no pullulan. The —·— lines in the figures refer to the control groups. Vertical bars on each line in the figures indicate the range of standard error.

As is clearly shown in FIGS. 1-A, B and C, the controlling effect on the increase in blood sugar content was largest in the second group which was fed with sucrose containing pullulan in a weight ratio of 1:100 of pullulan to sucrose.

The ratio of pullulan to sucrose and/or starch corresponding to an optimum controlling effect on the increase in blood sugar content varies within the aforementioned range because of factors such as the molecular weight of pullulan, and the age of person who is administered pullulan orally. For instance, in the case of pullulan having a molecular weight of 70,000, the optimum ratio of pullulan to sucrose and/or starch is 1:400.

EXAMPLE 7

The relationship between the age of the human subjects and the optimally effective weight ratio of pullulan as a hyperglycemia controlling agent was examined. Sugared water prepared by dissolving 25 g of sucrose in 500 ml of water was given to persons in two age groups, 41–49 years (FIG. 2-A) and 20–28 (FIG. 2-B) respectively. The results are shown in FIGS. 2-A, B. The largest controlling effect on the increase in blood sugar content was exhibited at the ratio of 1:50 of pullulan to sucrose for the first group, and at the ratio of 1:25 of pullulan to sucrose for the second group, respectively.

In FIGS. 2-A, B, the —·— lines show the change of blood sugar content over time for persons in the respective age groups who were orally administered 25 g of sucrose with no pullulan added thereto.

EXAMPLE 8

30 totally healthy persons (age 20–49) participated as subjects in the following experiments which were all conducted in the morning after an overnight fast.

Orange juice was the foodstuff product used in these experiments, more specifically, two kinds of orange juice containing 5 g and 10 g of sucrose per 100 ml, respectively. Pullulan of a molecular weight of 17,500 was added to the two kinds of orange juice in a proportion of 0.2 g per 100 ml, resulting in a weight ratio of pullulan to sucrose of 1:25 and 1:50, respectively. The pullulan-containing orange juices were boiled for sterilization, and then cooled in a refrigerator at 10° C. A given amount of the cooled orange juices was consumed by each of the 30 subjects over 10 minutes. Also, in control experiments conducted two days before, the same amount of the two kinds of orange juices containing the same amount of sucrose respectively, was administered to the same subjects.

Blood samples of 2 ml were taken from a forearm vein at 0, 15, 30 and 60 minutes after the orange juice was consumed by the subjects.

The mean fasting blood sugar content of the subjects was 86 mg/100 ml. The blood sugar content reached 100 and 82 mg/ml, respectively, 30 and 60 minutes after the orange juice containing 5 g/100 ml sucrose was consumed. In contrast, when orange juice containing pullulan in a weight ratio of 1:25 pullulan to sucrose was consumed, the blood sugar content after 30 and 60 minutes was 82 and 77 mg/ml, respectively.

The blood sugar content in subjects who were administered the orange juice containing 10 g/100 ml sucrose was 129 and 85 mg/ml at 30 and 60 minutes after intake, respectively. When the same subjects were administered orange juice to which pullulan had been added in a weight ratio of 1:50 of pullulan to sucrose, their blood sugar content was only 85 and 72 mg/ml at 30 and 60 minutes after intake, respectively.

The above experiments confirm that pullulan exhibits a remarkable inhibiting effect on the increase of blood sugar content arising from the intake of foodstuff, when pullulan is added to such foodstuff. Similar effects can be obtained with the addition of pullulan to any other foodstuff which contains starch, sucrose or mixtures thereof.

It is possible according to this invention to control in a safe manner the increase in blood sugar content which usually arises from intake of sucrose and/or starch. Therefore, this invention is useful in preventing obesity in a normal person, as well as in implementing the diet therapy of a diabetic person.

This invention is easy to practice in that pullulan can be added to foodstuff at the time of intake, or it can be incorporated into the foodstuff at the food processing stage. Therefore, the scope of application of this invention is broad, and it will contribute greatly to social welfare.

I claim:

1. A method of inhibiting the increase in blood sugar content which usually arises from the intake of foodstuff containing sucrose, starch and mixtures thereof, comprising adding pullulan to said foodstuff in a weight ratio of pullulan to sucrose, starch and mixtures thereof in the range of 1:400 to 1:20.

* * * * *